US011529469B2

United States Patent
Lee et al.

(10) Patent No.: US 11,529,469 B2
(45) Date of Patent: Dec. 20, 2022

(54) SUPPORT STRUCTURE

(71) Applicant: SHL MEDICAL AG, Zug (CH)

(72) Inventors: Wen-Yen Lee, Taoyuan (TW); Hsueh-Yi Chen, Taipei (TW)

(73) Assignee: SHL MEDICAL AG, Zug (CH)

( * ) Notice: Subject to any disclaimer, the term of this patent is extended or adjusted under 35 U.S.C. 154(b) by 322 days.

(21) Appl. No.: 16/954,715

(22) PCT Filed: Dec. 5, 2018

(86) PCT No.: PCT/EP2018/083705
§ 371 (c)(1),
(2) Date: Jun. 17, 2020

(87) PCT Pub. No.: WO2019/137701
PCT Pub. Date: Jul. 18, 2019

(65) Prior Publication Data
US 2020/0384202 A1 Dec. 10, 2020

(30) Foreign Application Priority Data

Jan. 9, 2018 (EP) ..................................... 18150688

(51) Int. Cl.
*A61M 5/315* (2006.01)
*A61M 5/32* (2006.01)
*A61M 5/28* (2006.01)

(52) U.S. Cl.
CPC .......... *A61M 5/31511* (2013.01); *A61M 5/28* (2013.01); *A61M 5/3257* (2013.01); *A61M 2209/08* (2013.01)

(58) Field of Classification Search
CPC .. A61M 5/31511; A61M 5/28; A61M 5/3257; A61M 5/31501; A61M 2005/208; A61M 2005/2407; A61M 2005/2411; A61M 2005/2437; A61M 2005/3261; A61M 2209/08

See application file for complete search history.

(56) References Cited

U.S. PATENT DOCUMENTS 5,947,929 A * 9/1999 Trull ................. A61M 5/14546
604/152
2017/0304548 A1* 10/2017 Chen .................... A61M 5/3202

FOREIGN PATENT DOCUMENTS

JP    2013-526904 A    6/2013
JP    2014-525315 A    9/2014
(Continued)

OTHER PUBLICATIONS

International Search Report and Written Opinion for Int. App. No. PCT/EP2018/083705, completed Jan. 8, 2019.

*Primary Examiner* — Nathan R Price
*Assistant Examiner* — Justin L Zamory
(74) *Attorney, Agent, or Firm* — McDonnell Boehnen Hulbert & Berghoff LLP

(57) ABSTRACT

A support structure for a medicament container is disclosed that is arranged to accommodate an elongated plunger rod, where the support structure has at least one flexible element arranged to be moved in contact with, and to exert a force, on a distal end surface of the medicament container, wherein the at least one flexible element is provided with a contact member arranged to contact an outer surface of the plunger rod and to be moved out of contact with the plunger rod when moved in contact with the medicament container.

11 Claims, 4 Drawing Sheets

(56) References Cited

FOREIGN PATENT DOCUMENTS

| | | |
|---|---|---|
| WO | 2011/123024 A1 | 10/2011 |
| WO | 2011/162686 A1 | 12/2011 |
| WO | 2016/055295 A1 | 4/2016 |
| WO | 2017/191159 A1 | 11/2017 |

* cited by examiner

SUPPORT STRUCTURE

CROSS REFERENCE TO RELATED APPLICATIONS

The present application is a U.S. National Phase Application pursuant to 35 U.S.C. § 371 of International Application No. PCT/EP2018/083705 filed Dec. 5, 2018, which claims priority to European Patent Application No. 18150688.2 filed Jan. 9, 2018. The entire disclosure contents of these applications are herewith incorporated by reference into the present application.

TECHNICAL FIELD

The present application relates to a support structure for a medicament container for the purpose of holding the medicament container in a steady state inside a medicament delivery device.

BACKGROUND

Regarding medicament delivery devices having a medicament container assembled therein, it is often a desire that the medicament container is supported such that it may not rattle or move inside the housing of the medicament delivery device. Due to tolerance variations of both the medicament container and the medicament delivery device as such, any support for a medicament container should preferably be flexible and possibly also resilient in order to handle forces exerted on the medicament delivery device and thus the medicament container if it e.g. is dropped onto a hard surface.

The document WO 2011/123024 discloses a medicament delivery device provided with a number of automatic functions, which medicament delivery device has been very well received on the market. The medicament delivery device comprises a support structure in the form of arc-shaped flexible elements that are to come in contact with a distal end surface of a medicament container placed in the medicament delivery device. The support structure then exerts a force in the proximal direction of the medicament container for preventing movement of the medicament container.

In most instances this solution works very well. However, there have been instances where the medicament container delivered have had dimensions outside the specification that the medicament delivery device was designed for, and most notably there has been variations in the radius measures of the transition surface between the inner surface of the barrel of the medicament container and the distally directed surface of the flange at the distal end of the medicament container. For batches of medicament containers having large radiuses, there is a risk that the arc-shaped support structures enter into the passage of the medicament container between its inner surface and the plunger rod, thereby risking a jamming of the plunger rod and thereby a malfunction of the medicament delivery device.

SUMMARY

The aim of the present disclosure is to remedy the drawbacks of the state of the art solutions.

This aim is solved with a support structure comprising the features of the independent patent claims. Preferable embodiments form the subject of the dependent patent claims.

According to a main aspect, a support structure is provided for a medicament container, which support structure is arranged to accommodate an elongated plunger rod. The support structure comprises at least one flexible element arranged to be moved in contact with, and to exert a force, on a distal end surface of the medicament container for reducing or eliminating movement of the medicament container. The at least one flexible element may be provided with a contact member arranged to contact an outer surface of the plunger rod and to be moved out of contact with the plunger rod when moved in contact with the medicament container.

The contact members will ensure that the flexible elements are securely guided generally radially outwards, both when a plunger rod is provided with the support structure, and also when a medicament container is arranged in contact with the flexible elements. Thus, any risk of jamming action of the flexible elements between the plunger rod and an inner surface of the medicament container is minimised.

According to one feasible aspect, the support structure may comprise a generally tubular body, into which body the plunger rod may be placed and wherein the at least one flexible element is arranged at one end of the tubular body. Further, the at least one flexible element may be flexible in a generally radial direction as well as in a generally axial direction.

According to a favourable solution, the at least one flexible element may comprises an arc-shaped structure extending in an inclined direction in relation to the longitudinal direction of the body and wherein inwardly directed surfaces of said arc-shaped structure are provided with inwardly directed protrusions. The protrusions will then ensure that the flexible elements are securely guided outwards when in contact with the medicament container. In this regard, the inwardly directed protrusions may bee provided with at least one inclined surface as seen in a plane parallel with the longitudinal direction of the body. More preferably, the inwardly directed protrusions may have a triangular shape with inclined surfaces as seen in a plane parallel with a longitudinal axis of the support structure. This ensures a very low friction between the contact members and the plunger rod when the plunger rod is inserted into the support structure.

In order to further reinforce the flexible elements, outwardly directed surfaces of the arc-shaped structure may be provided with outwardly directed protrusions.

These and other aspects of, and advantages with, the present application will become apparent from the following detailed description and the drawings.

BRIEF DESCRIPTION OF THE DRAWINGS

In the following description of the application, reference will be made to the accompanying drawings, of which

DETAILED DESCRIPTION

Figure 1:
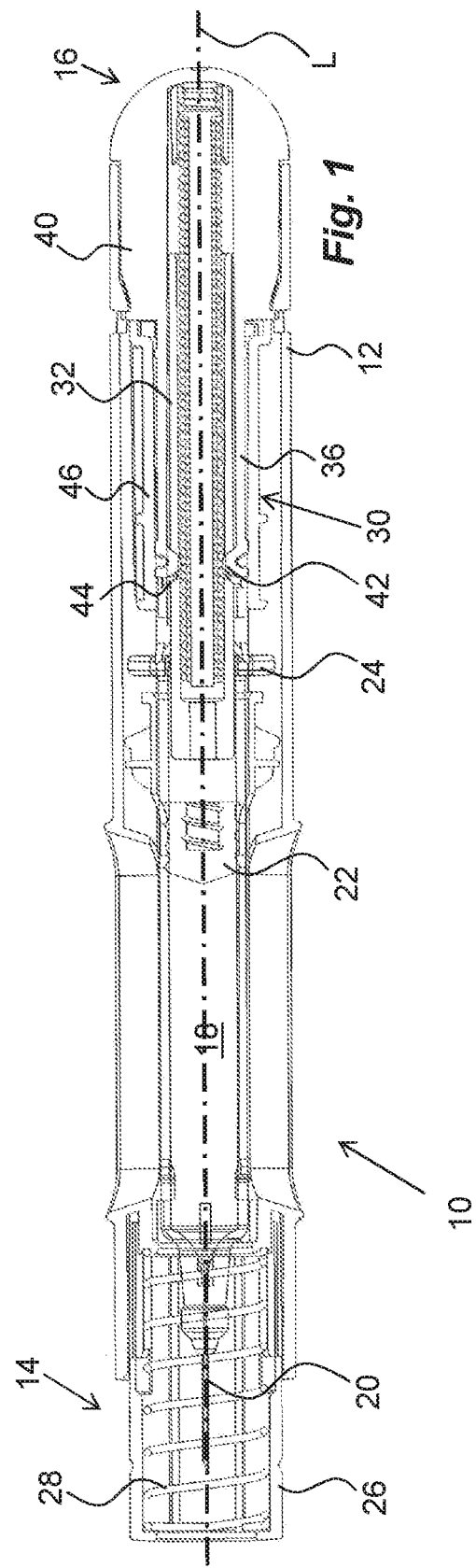
FIG. 1 is a cross-sectional view of a medicament delivery device that may utilize the solution according to the present application.

FIG. 1 shows an example of a medicament delivery device in which the support structure according the present application may be utilized. The medicament delivery device 10 comprises an elongated housing 12 having a proximal end 14 and a distal end 16 and extending along a longitudinal axis L. The interior of the housing is arranged to accommodate a medicament container 18. The medicament container 18 shown is provided with an integrated needle 20 and has a movable stopper 22 inside the tubular body thereof. The distal end of the medicament container 18 is arranged with a radially extending flange 24. The proximal end of the housing 12 is further arranged with a generally tubular medicament delivery member guard 26 that is movable between and extended position, as shown, covering the needle 20, and a retracted position wherein a penetration may be performed with the needle 20. The medicament delivery member guard 26 is preferably urged in the proximal direction by a medicament delivery member guard spring 28. The distal end of the housing 12 is provided with a power pack 30 comprising an elongated plunger rod 32 that is arranged to act on the stopper 22 for delivering a dose of medicament through the needle 20. The plunger rod 32 is driven by a compression spring 34.

The plunger rod 32 is held with the spring 34 in a tensioned state by radially flexible arms 36 on a generally tubular body 38 of a rear cap 40, which forms a support structure. The arms 36 are provided with inwardly directed protrusions 42 that fit into recesses 44 of the plunger rod 32. The arms 36 are prevented from releasing the plunger rod 32 by a generally tubular rotator 46 positioned radially outside the arms 36 with inner surfaces of the rotator 46 in contact with outer surfaces of the arms 36. The rear cap 40 is attached to the distal end of the housing 12, wherein the distal end of the spring 34 is abutting the rear cap 40.

In order to activate the medicament delivery device, the medicament delivery member guard 26 is pushed in the distal direction. The distal part of the medicament delivery member guard 26 is arranged with elements that are capable of turning the rotator 46 such that it is no longer in contact with the arms 36. Thus the arms 36 are free to move radially outwards and thereby release the plunger rod 32 for a dose delivery sequence.

The rear cap 40 is further arranged with elements 48 that are flexible in a generally longitudinal direction and that are designed to exert a force on a distal end of the medicament container 18 when the medicament container 18 is inserted into the medicament delivery device. In the embodiment shown, the flexible elements 48 comprise two generally arc-shaped structures that are somewhat outwardly inclined in relation to the longitudinal axis of the medicament delivery device.

Figure 2:
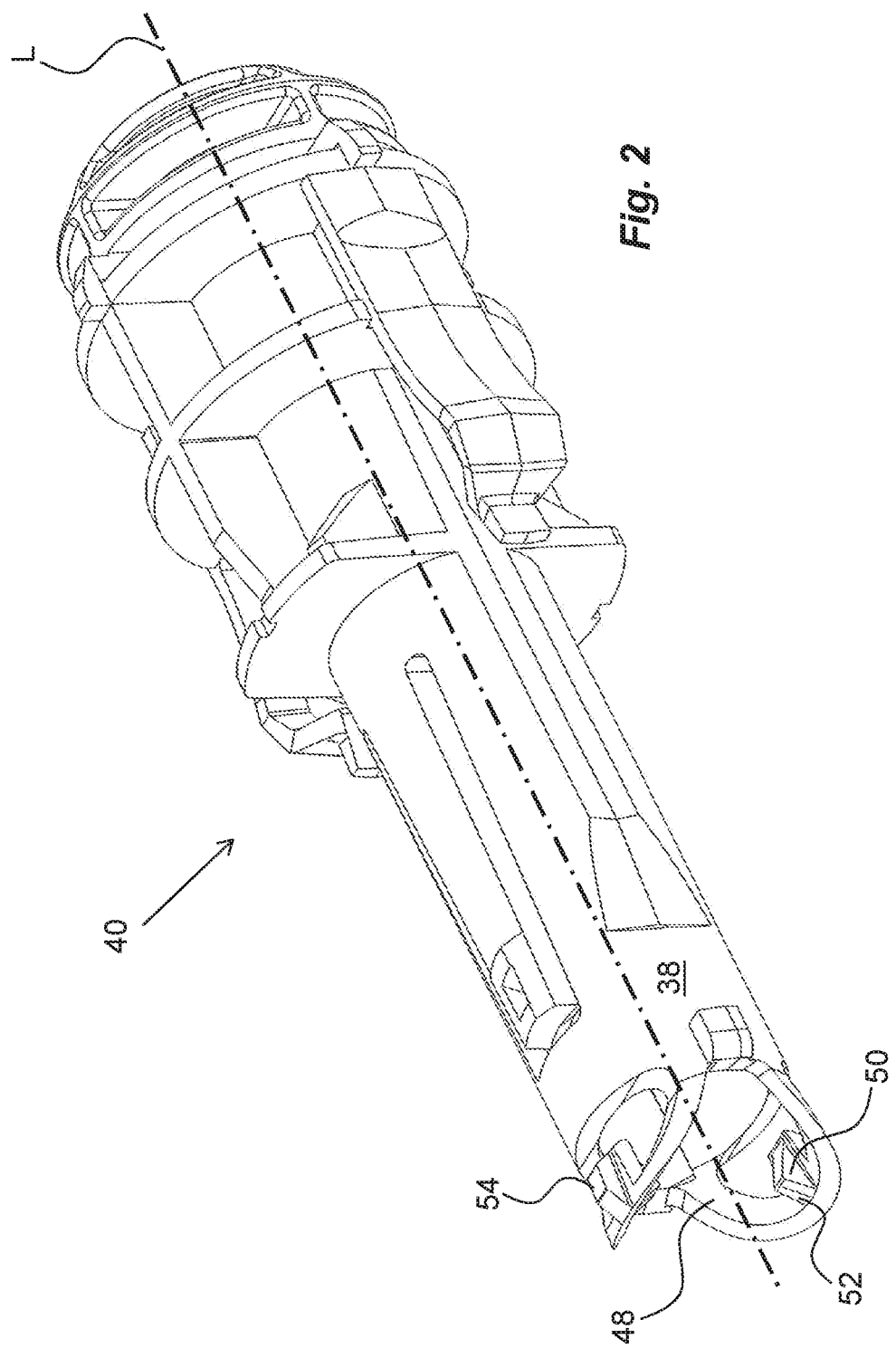
FIG. 2 is a perspective view of a support structure comprised in the medicament delivery device according to FIG. 1.

According to the application, the flexible elements 48 are arranged with contact members 50 that are to be in contact with the distal end of the medicament container 18 and in particular the flange 24 of the medicament container 18. The contact members 50 are in the shown embodiment inwardly directed protrusions that are integral with the inner surfaces of the flexible elements 48 as seen in FIG. 2. In the embodiment shown, the contact members 50 have a triangular shape as seen in a plane along the longitudinal axis, whereby one surface 52 is directed inclined in the proximal direction. Further, outwardly directed protrusions 54 are arranged on the flexible elements 48, reinforcing the outer part of the arc-shaped flexible elements 48.

Figure 3:
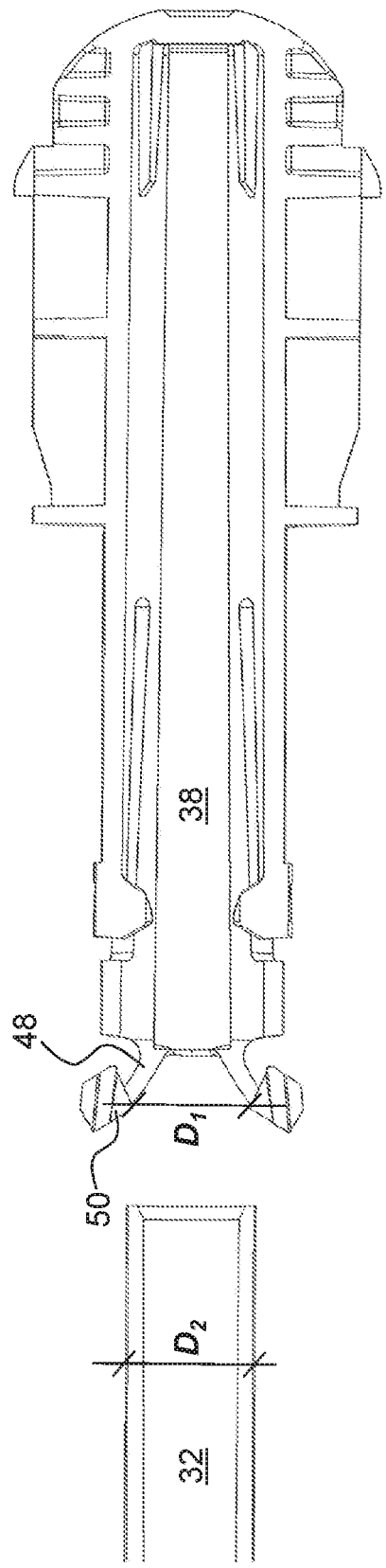
FIG. 3 is a cross-sectional view of different functional positions of the support structure of FIG. 2.
Figure 4:
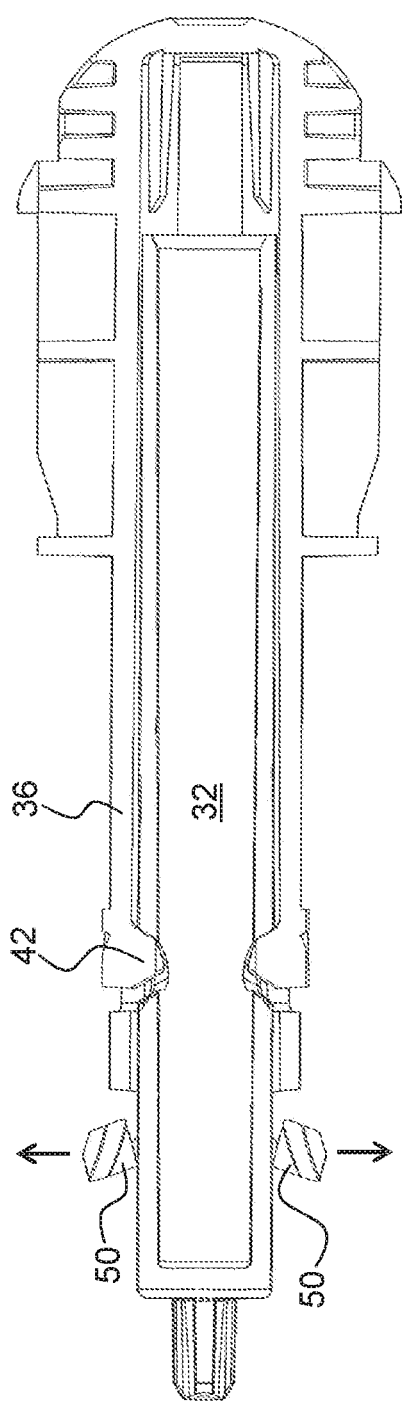
FIG. 4 is a cross-sectional view of different functional positions of the support structure of FIG. 2.

The support structure is intended to function as follows. As seen in FIG. 3, when no plunger rod 32 has yet been introduced into body 38 of the rear cap 40, the flexible elements 48 with the contact members 50 have such an inclination and design that the distance D1 between the innermost surfaces of the contact members 50 is somewhat smaller than the outer diameter D2 of the plunger rod. Thus, as seen in FIG. 4, when the plunger rod is inserted into the rear cap, the contact members will come in contact with the outer surface of the plunger rod and the flexible elements 48 will flex outwards. The triangular shape of the contact members 50 will provide point contact with the plunger rod 32 and thus a very low friction between the contact members 50 and the plunger rod 32.

Figure 5:
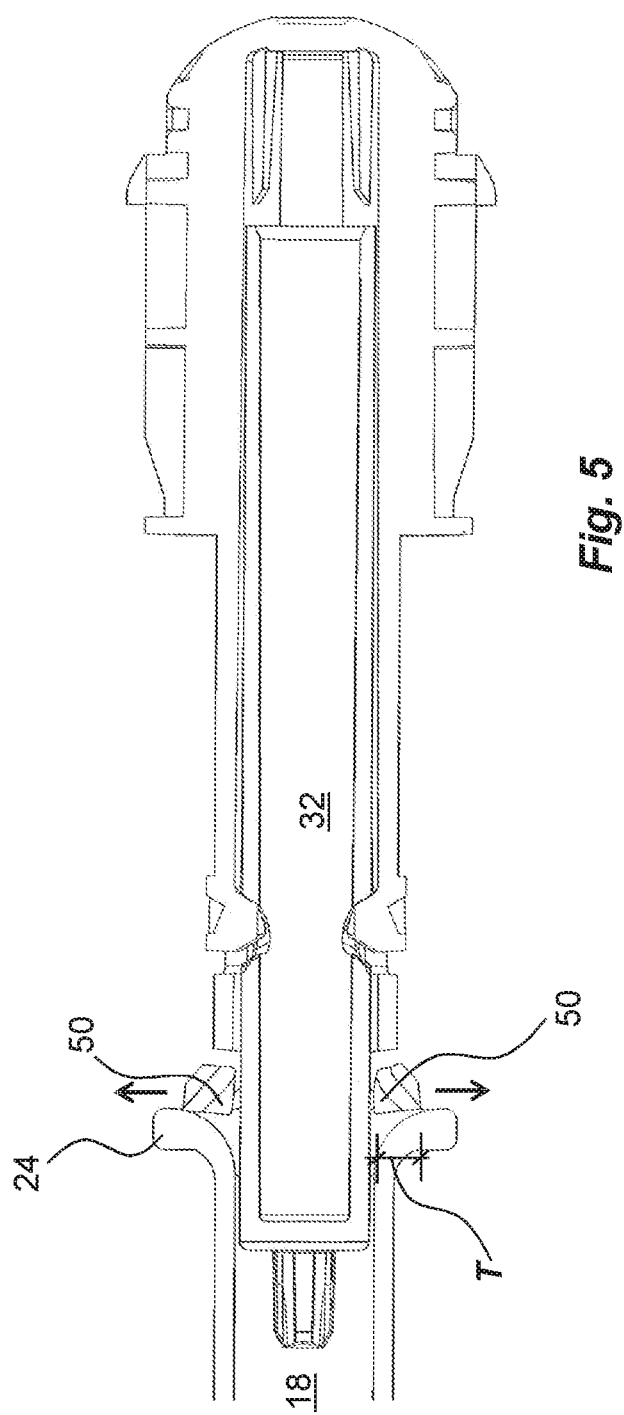
FIG. 5 is a cross-sectional view of different functional positions of the support structure of FIG. 2.

When now the rear cap 40 with the plunger rod 32 is assembled with the medicament container 18 inside the housing 12 of the medicament delivery device 10, the flexible elements 48 with the contact members 50 will come in contact with the distal end surface of the medicament container 18 and will flex radially, FIG. 5. Due to the increased thickness T of the flexible elements with the contact members 50 in the generally radial direction, an outward flexing is ensured and any jamming of the flexible elements 48 between the plunger rod 32 and the inner wall of the medicament container 18 is prevented. The outwards flexing action of the flexible elements 48 will further cause the contact members 50 to be moved out of contact with the plunger rod 32, FIG. 5, which will ensure that there is no friction at all from the contact members 50 during a subsequent dose delivery sequence when the plunger rod 32 is urged in the proximal direction, acting on the medicament container 18 for expelling a dose of medicament.

It is to be understood that the embodiment described above and shown in the drawings is to be regarded only as a non-limiting example of the application and that it may be modified in many ways within the scope of the patent claims.

The invention claimed is:

1. A support structure for a medicament container, which support structure is arranged to accommodate an elongated plunger rod, said support structure comprising:
   a distal end terminating at a rear cap that is configured to attach to and close an open distal end of an elongated housing of a medicament delivery device;
   at least one flexible element arranged to be moved in contact with, and to exert a force, on a distal end surface of said medicament container; and
   a generally tubular body, into which body said plunger rod may be placed,
   wherein said at least one flexible element is flexible in a generally radial direction as well as in a generally axial direction and is arranged at one end of said tubular body,
   wherein said at least one flexible element is provided with a contact member, where the contact member comes into contact with an outer surface of the plunger rod when the plunger rod is positioned in the tubular body, where when the at least one flexible element contacts the distal end surface of the medicament container the at least one flexible element will flex radially outward, and
   wherein when the at least one flexible element flexes radially outward the contact member will move out of contact with the plunger rod.

2. The support structure according to claim 1, wherein said at least one flexible element comprises an arc-shaped structure extending in an inclined direction in relation to the longitudinal direction (L) of the body and wherein inwardly directed surfaces of said arc-shaped structure are provided with inwardly directed protrusions.

3. The support structure according to claim 2, wherein said inwardly directed protrusions are provided with at least one inclined surface as seen in a plane parallel with the longitudinal direction (L) of said body.

4. The support structure according to claim 2, wherein said inwardly directed protrusions have a triangular shape with inclined surfaces as seen in a plane parallel with a longitudinal axis of said support structure.

5. The support structure according to claim 3, wherein outwardly directed surfaces of said arc-shaped structure are provided with outwardly directed protrusions.

6. A medicament delivery device comprising the support structure according to claim 1.

7. A support structure for a medicament container positioned within a medicament delivery device, the support structure comprising:
   a tubular body;
   a distal end terminating at a rear cap that is configured to attach to and close an open distal end of an elongated housing of a medicament delivery device;
   at least two flexible elements positioned at a proximal end of the tubular body and separated a distance to accommodate axial movement of an elongated plunger rod within the tubular body, where the at least two flexible elements are configured to be moved in contact with, and to exert a force, on a distal end surface of the medicament container;
   wherein the at least two flexible elements are radially flexible and axially flexible,
   wherein each of the at least two flexible elements comprises a contact member that engages an outer surface of the plunger rod such that the at least two flexible elements flex radially outward,
   wherein when the contact members engage the distal end surface of the medicament container the flexible elements continue flex radially outward causing the contact members to disengage from the outer surface of the plunger rod.

8. The support structure according to claim 7, wherein the at least two flexible elements further comprise arc-shaped structures extending in an inclined direction in relation to a longitudinal direction of the tubular body and wherein inwardly directed surfaces of the arc-shaped structures are provided with inwardly directed protrusions.

9. The support structure according to claim 8, wherein the inwardly directed protrusions are provided with an inclined surface that is part of a plane parallel with the longitudinal direction.

10. The support structure according to claim 9, wherein the inwardly directed protrusions have a triangular shape.

11. The support structure according to claim 10, wherein outwardly directed surfaces of the arc-shaped structure are provided with outwardly directed protrusions.

\* \* \* \* \*